(12) United States Patent
Yurkshtovich et al.

(10) Patent No.: US 10,806,732 B2
(45) Date of Patent: Oct. 20, 2020

(54) STABLE ANTI-NEOPLASTIC PHARMACEUTICAL COMPOSITION COMPRISING TEMOZOLOMIDE AND METHOD OF PREPARING THE COMPOSITION

(71) Applicant: DOUBLE BOND PHARMACEUTICAL AB, Uppsala (SE)

(72) Inventors: Mikalai Yurkshtovich, Minsk (BY); Dzmitry Veyeunik, Minsk (BY); Valiantsina Alinouskaya, Minsk (BY); Natalia Atrakhimovich, Minsk (BY); Iryna Halouchyk, Minsk (BY); Sergey Beliaev, Minsk (BY); Tatjana Yurkshtovich, Minsk (BY); Pavel Bychkouski, Minsk (BY); Aliaksandr Fedulau, Minsk (BY); Tatsiana Trukhachova, Minsk (BY)

(73) Assignees: Double Bond Pharmaceutical AB, Uppsal;a (SE); Research Institute of Physical Chemical Problems of the Belarulsna State University, Minsk (BY)

( * ) Notice: Subject to any disclaimer, the term of this patent is extended or adjusted under 35 U.S.C. 154(b) by 0 days.

(21) Appl. No.: 16/098,524

(22) PCT Filed: Apr. 28, 2017

(86) PCT No.: PCT/SE2017/050418
§ 371 (c)(1),
(2) Date: Nov. 2, 2018

(87) PCT Pub. No.: WO2017/192088
PCT Pub. Date: Nov. 9, 2017

(65) Prior Publication Data
US 2019/0142824 A1    May 16, 2019

(30) Foreign Application Priority Data

May 2, 2016 (EA) .............................. 201600400/26
May 2, 2016 (SE) .................................... 1600150-5

(51) Int. Cl.
*A61K 31/495* (2006.01)
*A61K 47/38* (2006.01)
(Continued)

(52) U.S. Cl.
CPC .......... *A61K 31/495* (2013.01); *A61K 9/0024* (2013.01); *A61K 9/0085* (2013.01);
(Continued)

(58) Field of Classification Search
CPC .. A61K 31/495; A61K 9/0024; A61K 9/0085; A61K 9/06; A61K 9/19;
(Continued)

(56) References Cited

U.S. PATENT DOCUMENTS

2010/0184706 A1* 7/2010 Bachovchin ........... A61K 47/64
514/1.1
2012/0283304 A1 11/2012 Pullagurla et al.
(Continued)

FOREIGN PATENT DOCUMENTS

CN        1923197 A      3/2007
CN     100 588 399 C     2/2010
(Continued)

OTHER PUBLICATIONS

Li et al.: Molecular Modification of Polysaccharides and Resulting Bioactivities, https://onlinelibrary.wiley.com/doi/full/10.1111/1541-4337.12161.*
(Continued)

*Primary Examiner* — Hong Yu
(74) *Attorney, Agent, or Firm* — Polsinelli PC (57) ABSTRACT

An anti-neoplastic stable pharmaceutical composition comprising Temozolomide, high substituted polysaccharide
(Continued)

phosphate in salt form, and high substituted polysaccharide phosphate in acidic form, in particular in a weight ratio of from 5 to 20% Temozolomide to 30 to 80% of polysaccharide in salt form, the reminder up to 100% being polysaccharide in acidic form. The level of 5-aminomidazole-4-carboxamide is below 0.5% by weight of Temozolomide in both the composition and the formulation disclosed. Also disclosed is a hydrogel for intrathecal administration obtainable by contacting the composition with sterile water, a method of manufacture of the composition and uses of the composition and the gel.

23 Claims, 3 Drawing Sheets (51) Int. Cl.
- A61K 47/22 (2006.01)
- A61K 9/19 (2006.01)
- A61K 9/00 (2006.01)
- A61K 9/06 (2006.01)
- A61K 35/00 (2006.01)
- A61K 47/24 (2006.01)
- A61K 47/36 (2006.01)
- A61P 35/00 (2006.01)

(52) U.S. Cl.
CPC .............. *A61K 9/06* (2013.01); *A61K 9/19* (2013.01); *A61K 47/22* (2013.01); *A61K 47/24* (2013.01); *A61K 47/36* (2013.01); *A61K 47/38* (2013.01); *A61P 35/00* (2018.01)

(58) Field of Classification Search
CPC ........ A61K 47/24; A61K 47/36; A61K 47/22; A61K 47/38; A61K 35/00
See application file for complete search history.

(56) References Cited

U.S. PATENT DOCUMENTS

| | | | | |
|---|---|---|---|---|
| 2014/0088036 | A1* | 3/2014 | Lehn | A61K 31/7024 514/53 |
| 2016/0199392 | A1* | 7/2016 | Trieu | A61K 31/415 514/165 |

FOREIGN PATENT DOCUMENTS

| | | |
|---|---|---|
| RU | 2442586 C1 * | 2/2012 |
| WO | WO 2014/104671 A1 * | 7/2014 |

OTHER PUBLICATIONS

Iulia Karlsson, "Neurological Disorders & Stroke and Neurooncology", J. Neurol Disord., vol. 5, Issue 2 (Suppl), Apr. 24, 2017, p. 37.

* cited by examiner

STABLE ANTI-NEOPLASTIC PHARMACEUTICAL COMPOSITION COMPRISING TEMOZOLOMIDE AND METHOD OF PREPARING THE COMPOSITION

CROSS REFERENCE TO RELATED APPLICATIONS

This application is a National Phase filing under 35 U.S.C. § 371 of PCT/SE2017/050418 filed on Apr. 28, 2017; which in turn claims priority to Application No. 201600400/26 filed in Eurasia on May 2, 2016 and claims priority to Application No. 1600150-5 filed in Sweden on May 2, 2016. The entire contents of each application are hereby incorporated by reference.

FIELD OF THE INVENTION

The present invention relates to a stable pharmaceutical composition comprising the antineoplastic agent Temozolomide, to preparation and use thereof.

BACKGROUND OF THE INVENTION

Temozolomide (TMZ), 4-methyl-5-oxo-2,3,4,6,8-pentazabicyclo[4.3.0]nona-2,7,9-triene-9-carboxamide of Formula 1

(1)

is an antineoplastic alkylating agent for use in the treatment of brain malignant gliomas melanoma and other neoplastic diseases. TMZ pass the blood brain barrier and is spontaneously hydrolyzed to the active compound in CNS.

Dacarbazide (DTIC) is a similar drug, it is only metabolized in liver and more toxic than Temozolomide (TMZ). Both TMZ and DTIC are prodrugs and forms the same pharmacologically active compound 5-(3-dimethyl-1 triazenyl)imidazole-4-carboxamide (MTIC). 5-aminoimidazole-4-carboxamide (AIC) is an unwanted side metabolite that is formed in both TMZ and DTIC compositions. TMZ does not require metabolism to form the pharmacologically active compound MTIC whereas DTIC does.

Compositions of TMZ comprises a mixture of TMZ and sodium salt of dextran phosphate, and the impurity content of AIC in relation to TMZ is up to 0.3% at the time of manufacture, and the content increase to about 0.5% during storage on the shelf for 2 years.

In addition to per-oral administration TMZ can be administered intrathecal, as disclosed in, for instance in WO 2006/060464 A1.

TMZ penetrates well through the blood brain barrier, having, however, a very short half-life. TMZ is quickly absorbed upon oral administration, its peak plasma concentration is reached after 0.7 h, and its half-life is 1.8 h. In order to support the effective concentration of TMZ, e.g. in the brain, a repeated administration of the drug is required which is associated with a discomfort for the patients and causes a risk of toxic effects' manifestation.

BY 11838 C1 discloses a combined treatment method for malignant brain tumors. The method comprises surgical excision of the tumor tissue followed by application of TMZ comprised by high substituted dextran phosphate gel of pH 7.2-7.4. The dry weight ratio of TMZ/high substituted dextran phosphate in the preparation is 0.03:1.0. The freeze-dried gel is reconstituted by the addition of sterile water and pH adjusted prior to use, then applied to the wound surface. The pH adjustment is performed in the operation room does not provide enough precision and is time consuming. In addition, the structure of highly substituted dextran phosphate contains a large number of di- and tri-substituted phosphoric acid groups, which provide additional cross-linking of macromolecules, which reduces the ability to absorb water and limits the amount of TMZ to 30 mg/g in the gel of highly substituted dextran phosphate. The low concentration of TMZ in the composition implies that the volume must be increased to administrate higher dose of the substance, i.e., the prodrug TMZ, and thus also the amount highly substituted dextran phosphates administered is increased. A 2- or 3-fold increase in the amount of highly substituted dextran phosphates can lead to undesirable reactions associated with the duration of the biodegradation process. Moreover, as established by the authors, TMZ decomposes upon pH 7.2-7.4, being partially hydrolyzed with the formation of 5-aminoimidazole-4-carboxamide (AIC) in amounts exceeding permissible levels in relation to TMZ

OBJECTS OF THE INVENTION

A problem with the known composition is its content of 5-aminoimidazole-4-carboxamide (AIC) which increase above the limit of 0.5% by weight upon storage of the drug.

The present invention seeks to remedy this problem and provides a stable and reproducible pharmaceutical composition comprising Temozolomide and a method of preparing said composition.

SUMMARY OF THE INVENTION

The present invention therefore provides a stable anti-neoplastic pharmaceutical composition comprising or substantially consisting of Temozolomide (TMZ) and a mixture of polysaccharide phosphates in salt and acid forms. The present composition maintains the pH in the required interval, i.e. 4.5-7.0, thereby adjustment of pH is not needed when making the formulation to be used as other compositions described in prior art. Another very important advantage is that the composition is very stable and the amount of 5-aminoimidazole-4-carboxamide (AIC), an unwanted metabolite, is much lower compared to the compositions used today, and the amount does not increase upon storage.

A preferred form of the formulation comprises of 5 to 20% of TMZ by weight and of 95 to 80% of the mixture of polysaccharide phosphate in salt and acid forms by weight.

The present invention further provides a stable antineoplastic pharmaceutical formulation for intrathecal administration in the form of an aqueous gel. The composition comprises or substantially consists of TMZ and a mixture of polysaccharide phosphates in salt and acid forms. The weight ratio of the polysaccharide phosphates in salt:acid form is from about 1:0.4 to 5:1. In another embodiment the weight ratio of the polysaccharide phosphates in salt:acid form is 1:1 to 1:3.

It is preferred for the polysaccharide to be selected from the group consisting of dextran, starch, hemicellulose, cellulose, and mixtures thereof.

Most preferred is dextran. In particular, dextran has a molecular mass of from about 40 kDa to about 100 kDa. More preferred is dextran of a molecular mass of from 60 kDa to 70 kDa.

The salt form of polysaccharide phosphate is selected from the group consisting of sodium, potassium, ammonium, magnesium and calcium salt, or mixtures thereof. Sodium being most preferred.

According to a preferred aspect of the invention the weight ratio of TMZ to total polysaccharide phosphate in the composition is from 1:4 to 1:19. In particular the weight ratio of TMZ to total polysaccharide phosphate in the composition is about 1:9.

Another object of the invention further provides a first method of preparing the composition of the invention; the method comprises the steps of:
a) providing an aqueous solution of TMZ;
b) introducing a dry mixture of high substituted polysaccharide phosphate in salt form and of high substituted polysaccharide phosphate in acidic form to the TMZ solution;
c) freeze drying the obtained solution in step b) to obtain a precipitate; and
c) sterilizing the composition.

The amount TMZ is preferably in the range of 5-20% by weight.

The amount of the dry mixture of polysaccharide phosphate in the salt form and polysaccharide phosphate in the acidic form, wherein the salt form is preferably in the range of from 30 to 80% by weight and the rest up to 100% is in the acidic form.

The freeze drying may be performed by using cryo precipitation or lyophilization.

The sterilizaion may be performed by using any suitable method. Preferably by radiation.

The present invention further provides a second method for preparing a composition of the invention, the method comprises the steps of:
a) providing a mixture of high substituted polysaccharide phosphate in salt form and of high substituted polysaccharide phosphate in acidic form;
b) forming a hydrogel from the mixture by addition of an aqueous solvent;
c) freeze drying the gel;
d) adding powderous TMZ to the precipitate obtained in step c);
e) mixing the TMZ powder and precipitate;
f) optionally grinding the mixture of precipitate and TMZ to form a powderous composition;
g) optionally sterilizing the powderous composition.

The amount TMZ is preferably in the range of 5-20% by weight.

The amount the dry mixture of polysaccharide phosphate in the salt form and polysaccharide phosphate in the acidic form, wherein the salt form is preferably in the range of from 30 to 80% by weight and the rest up to 100% is in the acidic form.

The freeze drying may be performed by using cryo precipitation or lyophilization.

The sterilizaion may be performed by using any suitable method. Preferably by radiation.

The aqueous solvent used in the examples is water but may also be another pharmacologically acceptable liquid such as saline or phosphate buffer.

Another object of the present invention is to provide a pharmaceutical formulation in the form of a hydrogel for intrathecal administration. The hydrogel is formed by contacting the composition of the invention with an aqueous solvent. The aqueous solvent may be water but also other pharmacologically acceptable solvents such as saline or phosphate buffer can also be used.

The hydrogel is obtained by mixing 1 part by weight of the composition described above with 10-30 parts by weight of aqueous solvent.

A preferred embodiment of the hydrogel is obtained by mixing 1 part by weight of the composition described above with 10-15 parts by weight of sterile water. Most preferred is 1 part composition and 15 parts sterile water.

The AIC content of the formulation described above is less than 0.5% by weight or less, in particular 0.3% by weight or 0.1 by weight or less.

According to a further preferred aspect of the invention the hydrogel substantially consists of high substituted polysaccharide phosphate in salt form, high substituted polysaccharide phosphate in acidic form, TMZ, and water. The AIC content is about 0.01% by weight or less of TMZ. Most preferred is a formulation with no detectable amounts of AIC by HPLC. The formulation(s) can be prepared by adding an aqueous solvent to the composition obtainable by the first method, or by adding an aqueous solvent to the composition obtainable by the second method, both described above.

Also disclosed is the use of the pharmaceutical composition/formulation and of the hydrogel formed by contacting the composition with an aqueous solvent (i.e., formulation) in the treatment of cancer. In particular the cancer is localized to the brain, such brain tumours; Grade II-IV of malignancy, such as oligoastrocytoma, anaplastic astrocytoma, and glioblastoma.

The present invention provides a hydrogel comprising TMZ in the range of 0.5-5 mg/ml.

Finally, the present invention provides a method for treating cancer, wherein a formulation comprising the composition as defined by the present claim 1 is given to a subject in any suitable route of administration.

The method may be used as first line treatment or second line treatment or in combination with other methods. The formulation may also be implanted in a cavity caused by removal of a tumour.

The invention will now be described in more detail by reference to a number of preferred embodiments.

BRIEF DESCRIPTION OF DRAWINGS

FIG. 1 FIGS. 1a and 1b show HPLC-chromatograms of impurity level analysis of the AIC content of a TMX-polymeric composition (a), and of the TMX-composition of the present invention (b).

DETAILED DESCRIPTION

It is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

All references cited herein are incorporated by reference in their entirety and for all purposes to the same extent as if each individual publication or patent or patent application was specifically and individually indicated to be incorporated by reference in its entirety for all purposes.

The present invention is best understood by reference to the following definitions, the Figures and exemplary disclosure provided herein.

The maximum TMZ content in the declared pharmaceutical formulation (20% of the mass) was identified based on TMZ solubility in water or other pharmacologically acceptable solvents that are added to prepare the implant in a gel form. The lowest limit of TMZ content (5% of the mass) is due to the minimum efficacy of the declared pharmaceutical formulation.

The declared limits of the polysaccharide phosphate in the salt form content (from 30 to 80% of the mass) and the polysaccharide phosphate in the acidic form content (to 100% of the mass) in the declared pharmaceutical formulation are determined by the increase in the content of 5-aminoimidazole-4-carboxamide hydrochloride (USP Decarbazine Related Compound A), normalized within the limit of 0.5% of the mass for the authorized drug substance (TMZ). In the present pharmaceutical formulation the content of Decarbazine Related Compound A is less than 0.5% of the mass and down to 0.01% of the weight or even to quantities not detectable using HPLC.

Mass ratio of components of the declared pharmaceutical formulation was chosen experimentally, mainly according to the antineoplastic efficacy and storage stability using the following indicators: "Quantitative content of TMZ", "Decarbazine Related Compound A", "Water absorption", "Sterility".

EXAMPLE 1-5 Manufacture of high substituted dextran phosphate compositions comprising Temozolomid.

Example 1

100 g of dextran phosphate, obtained by using any known method, is placed into the reaction vessel, 5 L of distilled water is added, and the mixture is stirred until a homogenous suspension is formed. A 10% sodium hydroxide solution is added in portions into the obtained water suspension of dextran phosphate with stirring for 5 minutes and pH measuring after addition of each portion. Addition of 10% sodium hydroxide solution is stopped when pH of the reaction medium has settled at 6.0-7.0. The reaction mixture is then kept for 30 min at room temperature and lyophilized. The dextran phosphate content in the sodium form and the dextran phosphate content in the acidic form in the lyophilized product is 60 and 40% by weight, respectively.

10 gram of Temozolomide is added to 90 g of the obtained lyophilized powder consisting of the mixture of dextran phosphate in the salt and acidic forms, the dry mixture is thoroughly stirred, divided into 1 g portions and packed into any appropriate hermetically sealed package, and sterilized using gamma irradiation at the dose of 0.5 Mrad. The resulting composition comprises 10% by weight Temozolomide, 54% by weight dextran phosphate in the salt form and 36% by weight of dextran phosphate in the acidic form.

Example 2

80 g of cellulose phosphate, obtained by using any known method, is placed into the reaction vessel, 5 L of distilled water is added, and the mixture is stirred until a homogenous suspension is formed. A 10% sodium hydroxide solution is added in portions into the obtained water suspension of cellulose phosphate with stirring for 5 minutes and pH measuring after addition of each portion. Addition of 10% sodium hydroxide solution is stopped when pH of the reaction medium has settled at 6.0-7.0. The reaction mixture is then kept for 30 min at room temperature and lyophilized. The cellulose phosphate content in the sodium form and the cellulose phosphate content in the acidic form in the lyophilized product is 70 and 30% by weight, respectively.

20 gram of Temozolomide is added to 80 g of the obtained lyophilized powder consisting of the mixture of cellulose phosphate in the salt and acidic forms, the dry mixture is thoroughly stirred, placed in forming molds, pressurized, obtained sheets are placed in plastic bags, hermetically sealed and sterilized using gamma irradiation at the dose of 0.5 Mrad. The resulting formulation comprises 20% by weight Temozolomide, 56% by weight cellulose phosphate in the salt form and 24% by weight of dextran phosphate is the acidic form.

Example 3

100 g of dextran phosphate, obtained by using any known method, is placed into the reaction vessel, 5 L of distilled water is added, and the mixture is stirred until a homogenous suspension is formed. A 10% magnesium hydroxide solution is added in portions into the obtained water suspension of dextran phosphate with stirring for 5 minutes and pH measuring after addition of each portion. Addition of 10% magnesium hydroxide solution is stopped when pH of the reaction medium has settled at 6.0-7.0. The reaction mixture is then kept for 30 min at room temperature and lyophilized. The dextran phosphate content in the magnesium form and the dextran phosphate content in the acidic form in the lyophilized product is 80 and 20% by weight, respectively.

5 gram of Temozolomide is added to 95 g of the obtained lyophilized powder consisting of the mixture of dextran phosphate in the salt and acidic forms, the dry mixture is thoroughly stirred, divided into 1 g portions and packed into any appropriate hermetically sealed package, and sterilized using gamma irradiation at the dose of 0.5 Mrad. The resulting formulation comprises 5% by weight Temozolomide, 76% by weight dextran phosphate in the salt form and 19% by weight dextran phosphate in the acidic form.

Example 4

10 g Temozolomide is dissolved in 3 L sterile distilled water and 90 g of the mixture comprising 60% by weight dextran phosphate in the salt form and 40% by weight dextran phosphate in the acidic form. The mixture is stirred until a homogenous mixture is reached, thereafter lyophilized, and the dry mixture is thoroughly stirred, divided into 1 g portions and packed into any appropriate hermetically sealed package, and sterilized using gamma irradiation at the dose of 0.5 Mrad. The resulting formulation comprises 10% by weight Temozolomide, 54% by weight of the mass dextran phosphate in the salt form and 36% by weight of dextran phosphate in the acidic form.

Example 5

Preparation of the Pharmaceutical Formulation

The pharmaceutical formulation is obtained as in example 1, except for that the mixture of starch phosphate in salt from and the starch phosphate in acidic form is used. The composition of the declared pharmaceutical formulation is shown in table 1.

Figure 1:
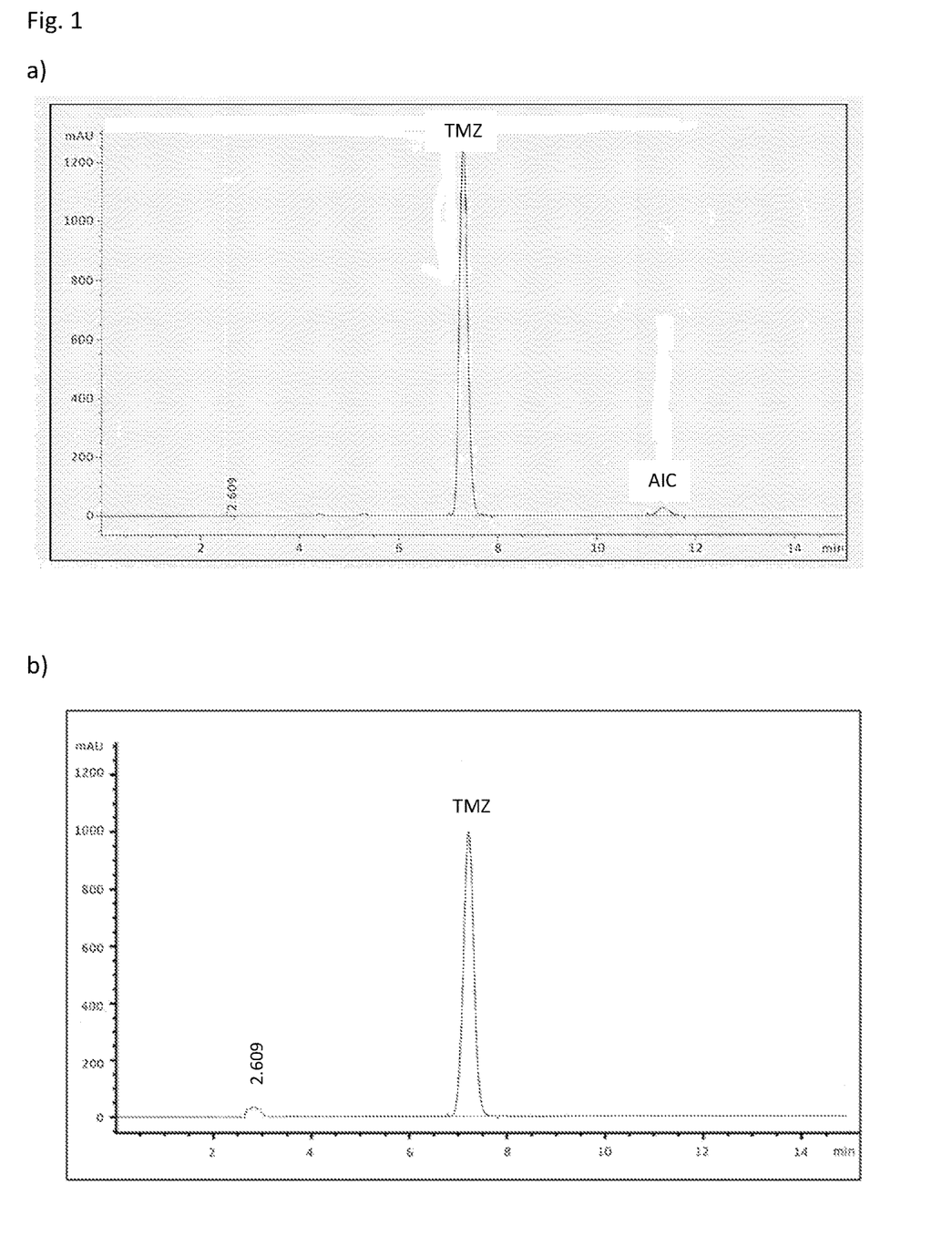

Temozolomide and AIC contents are determined using HPLC, See FIGS. 1a and 1b, respectively). The solution is prepared in the following way for the experiment: 0.2500 g of the experimental pharmaceutical formulation is introduced into a 25 mL volumetric flask, 20 mL of dimethyl sulfoxide is added, the mixture is treated with ultrasound for 15 min and the volume is adjusted with the same solvent up to the mark.

The resulting solution is filtered through a membrane filter with pore size of 0.45 μm. The solution is used freshly prepared.

Conditions of the chromatography: liquid chromatograph with the spectrophotometric detector set to 254 nm,
   a stainless steel 250×4.6 mm column filled with octadecyl silica gel for the chromatography with the particle size of 5 μm, for instance, Nucleodur C18 Gravity.

The rate of mobile phase—1 mL/min. Injected sample volume—10 μL.

Mobile phase: 0.846 g/L aqueous solution of sodium hexane sulfonate:methanol:glacial acetic acid in the ratio 895,5:100:4,5.

The sterility of the declared pharmaceutical formulation was determined using standard pharmaceutical methods.
   To determine absorption, a 0.2 g sample of the inventive pharmaceutical formulation was placed in 50 mL distilled water and kept for 1 h. Hydrogel was then separated from the excess of liquid on a glass filter and placed in pre-weighed weighing bottle, weighed and dried in a vacuum oven over the phosphorus oxide at 323° K until constant mass. Water absorption capacity of the inventive pharmaceutical formulation was calculated based on the mass difference between the swelled and dried sample.

The pharmaceutical formulation obtained using any of the above described methods can be used for the intrathecal injection, local administration or for the production of other drug formulations intended for oral administration.

Examples 6-8 Production of Oral Dosage Forms

Example 6

The pharmaceutical formulation obtained using any of the described methods in examples 1-5 is mixed at approximate amounts of 50 mg (calculation is made for 5 mg of Temozolomide content) with auxiliaries: lactose—90 mg, sodium carboxyl methyl starch—7.5 mg, colloidal silicone dioxide—0.2 mg, wine acid—3.0 mg. The resulting mixture is subjected to wet or dry granulation. The obtained granulate is filled into hard gelatine capsules. The drug is intended for oral use at a dose of 5 mg of Temozolomide.

Example 7

The pharmaceutical formulation obtained using any of the described examples 1-5 is mixed at approximate amounts of 500 mg (calculation is made for 50 mg of Temozolomide content) with auxiliaries: 55 mg of lactose, 15 mg of sodium carboxyl methyl starch, 10.0 mg of wine acid, 14 mg of stearic acid. The resulting mixture is subjected to wet or dry granulation, the obtained granulate is sent to pressing. The pills intended for oral use at a dose of 50 mg of Temozolomide are obtained.

Example 8

The pharmaceutical formulation obtained using any of the described examples 1-5 in the form of gel is mixed at approximate amounts of 2500 mg (calculation is made for 250 mg of Temozolomide content) with auxiliaries: lactose—180 mg, sodium carboxyl methyl starch—28 mg, wine acid—20 mg and subjected to wet granulation. The granules are dusted with calcium (or magnesium) stearate and packed into disposable packages. The drug is intended for a one-time oral use at a dose of 250 mg of Temozolomide.

Efficacy evaluation of the declared antineoplastic pharmaceutical formulation was made in a clinical setting on 41 patients (experimental group) with malignant (Grade II-IV) brain tumours. In the operation room, 15 ml of sterile water was added to 1 g of the declared pharmaceutical formulation containing 10% by weight Temozolomide, 54% by weight dextran phosphate in sodium form and 36% by weight dextran phosphate in acidic form and kept for 20-30 min until a homogenous dense mass is formed. The resulting mass was implanted into the resected tumour cavity.

Figure 2:
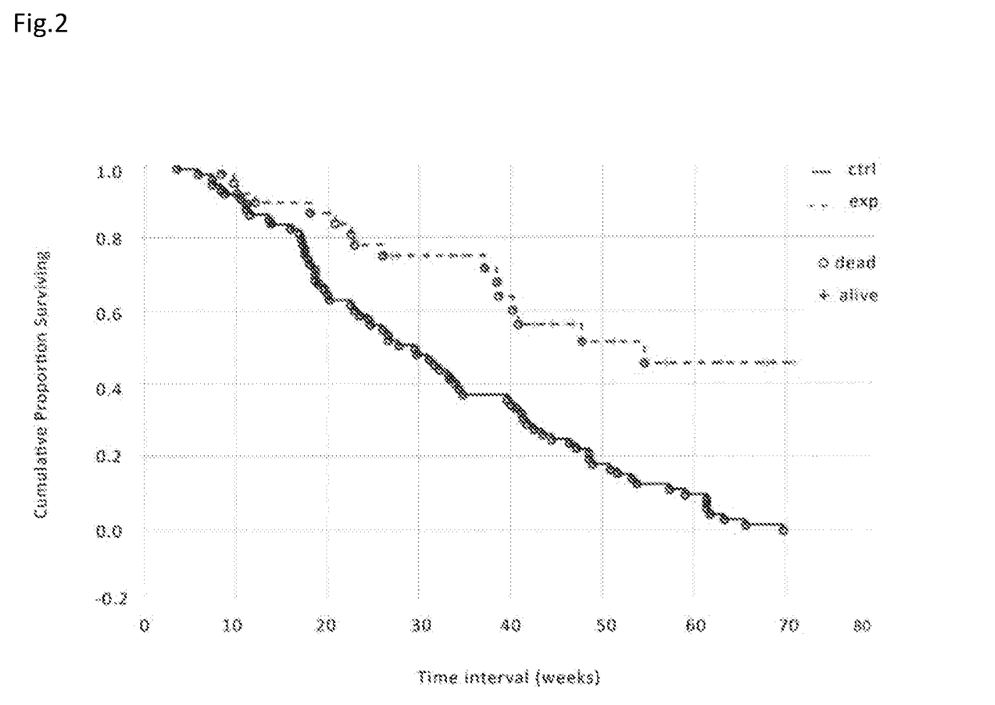
FIG. 2 Demonstrates postoperative survival of patients treated with the composition/formulation of the present invention and control group after a total removal of Grade II-IV brain tumours.
Figure 3:
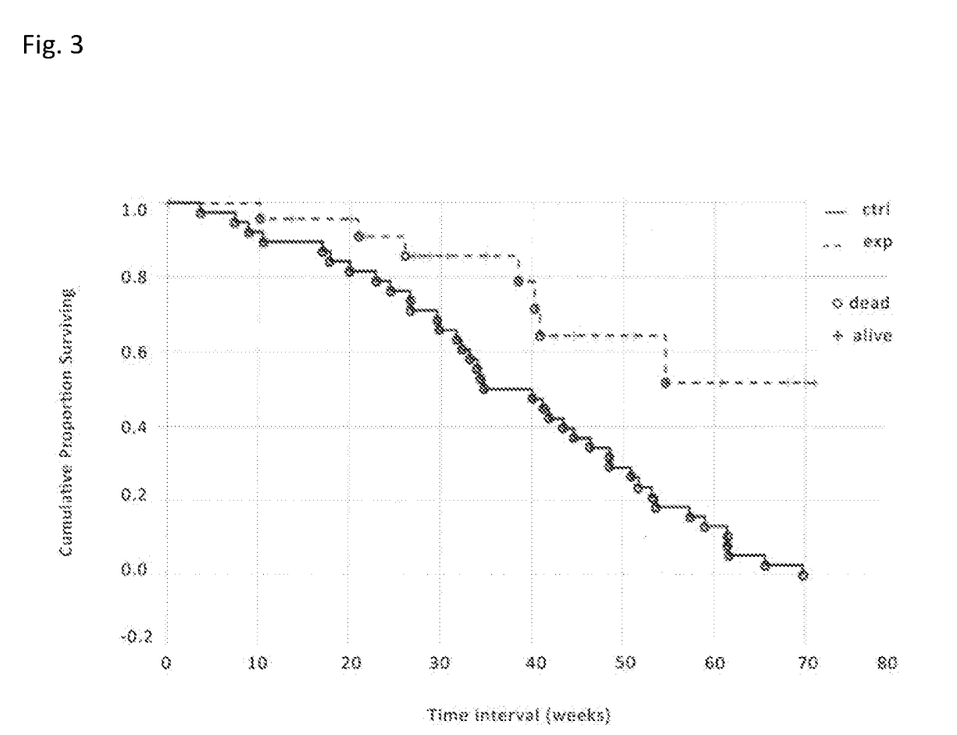
FIG. 3 Demonstrates the duration of the recurrence-free period for the patients treated with the composition/formulation of the present invention and control group with brain tumours.

FIGS. 2 and 3 present the results of the study. The use of the presently disclosed antineoplastic pharmaceutical formulation leads to a substantially increased mean length of life in patients with malignant brain tumours and decreases the risk of relapse.

Table 1 shows that the composition of the present innovation is stable during at least 2.5 years of storage and the amount of AIC is not increased during storage. The content of TMX, and AIC, amount of water absorption and sterility was measured and the results are shown in table 1 below.

TABLE 1

Composition of the declared antineoplastic pharmaceutical formulation and storage stability

| | | | Composition (% by weight) | | | Quality indicators at the production moment | | | | Quality indicators after 2.5 years of storage | | | |
|---|---|---|---|---|---|---|---|---|---|---|---|---|---|
| | | | | | | Content (% by weight) | | Water absorption | | Content (% by weight) | | Water absorption | |
| No. | PS | Salt | TMZ | PSP salt | PSP acid | TMZ | AIC | (g/g) | Sterility | TMZ | AIC | (g/g) | Sterility |
| 1 | dextran | Na | 10 | 54 | 36 | 10 | ND | 27 | sterile | 10 | ND | 27 | sterile |
| 2 | cellulose | Na | 20 | 56 | 24 | 20 | 0.12 | 28 | sterile | 20 | 0.13 | 28 | sterile |
| 3 | dextran | Mg | 5 | 76 | 24 | 5 | 0.18 | 21 | sterile | 5 | 0.18 | 21 | sterile |
| 4 | dextran | K | 10 | 54 | 36 | 10 | ND | 27 | sterile | 10 | ND | 27 | sterile |
| 5 | starch | Na | 10 | 54 | 36 | 10 | 0.28 | 34 | sterile | 10 | 0.28 | 34 | sterile |
| 6 | dextran | Na | 5 | 80 | 15 | 5 | 0.22 | 34 | sterile | 5 | | 34 | sterile |
| 7 | dextran | Ca | 10 | 54.8 | 35.2 | 10 | ND | 20 | sterile | 10 | ND | 20 | sterile |
| 8 | dextran | Na | 20 | 30 | 50 | 20 | 0.09 | 24 | sterile | 20 | 0.09 | 24 | sterile |
| 9 | starch | K | 5 | 64.5 | 30.5 | 5 | 0.15 | 28 | sterile | 5 | 0.15 | 28 | sterile |
| 10 | starch | Na | 10 | 68.8 | 21.2 | 10 | 0.28 | 35 | sterile | 10 | 0.28 | 35 | sterile |
| 11 | dextran | Na | 10 | 64.1 | 25.9 | 10 | 0.08 | 32 | sterile | 10 | 0.08 | 32 | sterile |

Abbreviations:
PS: Polysaccharide;
PSP-salt: Polysaccharide phosphate in salt form;
PSP-acid: Polysaccharide phosphate in acidic form,
TMZ: Temozolomide;
AIC: 5-aminomidazole-4-carbamide,
ND: Non-detectable

The invention claimed is:

1. A pharmaceutical composition having antineoplastic anti-neoplastic activity comprising from 5 to 20% by weight of Temozolomide based on the total weight of the composition, less than 0.5% by weight of 5-aminomidazole-4-carboxamide (AIC) relative to the weight of the Temozolomide, and a mixture of 30 to 80% by weight substituted polysaccharide phosphate in salt form based on the weight of the mixture and the reminder up to 100% by weight of substituted polysaccharide phosphate in acidic form based on the weight of the mixture.

2. The composition of claim 1, wherein the polysaccharide phosphate is selected from the group of dextran, starch, cellulose, and mixtures thereof.

3. The composition of claim 2 wherein the polysaccharide is dextran.

4. The composition of claim 3, wherein the dextran has a molecular mass of 40 to 100 kDa.

5. The composition of any of claim 1, wherein the salt is selected from the group of salts of sodium, ammonium, potassium, magnesium and calcium and mixtures thereof.

6. The composition of claim 5, wherein the salt is a sodium salt.

7. The composition of claim 1, wherein the weight ratio of Temozolomide to total polysaccharide phosphate is from 1:4 to 1:19.

8. The composition of claim 7, wherein the weight ratio is about 1:9.

9. The composition of claim 1, wherein the weight ratio of polysaccharide phosphate in salt form to polysaccharide phosphate in acidic form is from 30:65 to 80:15.

10. The composition of claim 9, wherein the weight ratio of polysaccharide phosphate in salt form to polysaccharide phosphate in acidic form is about 55:35.

11. A method for preparing a pharmaceutical composition as defined in claim 1, comprising the steps of:
    a) providing an aqueous solution of Temozolomide;
    b) introducing a dry mixture of substituted polysaccharide phosphate in salt form and of high substituted polysaccharide phosphate in acidic form to the Temozolomide solution;
    c) freeze drying the obtained solution in step b) to obtain a precipitate; and
    d) sterilizing the composition.

12. A method for preparing a pharmaceutical composition as defined in claim 1, comprising the steps of:
    a) providing a mixture of substituted polysaccharide phosphate in salt form and of substituted polysaccharide phosphate in acidic form, wherein the salt form is in the range of 30-80% by weight of the mixture and the rest up to 100% is in the acidic form;
    b) forming a hydrogel comprising the mixture of the polysaccharide phosphates by adding an aqueous solvent;
    c) freeze drying the gel;
    d) adding powderous Temozolomide to the precipitate obtained in the foregoing step;
    e) mixing the Temozolomide powder and precipitate, and
    f) optionally sterilizing the powderous composition.

13. A pharmaceutical formulation in an administration form for local, intrathecal, implantation, or oral administration, said formulation comprising the composition of claim 1, and optionally at least one auxiliary agent.

14. A pharmaceutical formulation in the form of a powder, granules, suspension, emulsion, capsules, micro pellets, pills, sheet/wafers for gel preparation, hydrogel, a ready to use gel or a transdermal patch, said formulation comprising the formulation of claim 13.

15. A hydrogel comprising the composition defined in claim 1, wherein the amount of Temozolomide is in the range of 0.5-5 mg/ml.

16. The hydrogel of claim 15, prepared by mixing 1 part by weight of said composition with 10-30 parts by weight of an aqueous solvent.

17. The composition of claim 1 or formulation thereof in an administration form for local, intrathecal, implantation, or oral administration, said formulation comprising said composition and optionally at least one auxiliary agent for use in the treatment of cancer.

18. The composition or the formulation for use according to claim 17, wherein the cancer is brain cancer.

19. A hydrogel according claim 15 for use in intrathecal administration in the treatment of cancer.

20. A method for the treatment of cancer, comprising administrating a therapeutically effective amount of the pharmaceutical composition of claim 1 or the formulation thereof in an administration form for local, intrathecal, implantation, or oral administration, said formulation comprising said composition and optionally at least one auxiliary agent.

21. The method for the treatment of cancer according to claim 20, wherein the cancer is brain cancer.

22. The method according to claim 20, wherein the administration is by local, intrathecal, or implantation administration.

23. The composition of claim 1, having a pH of 4.5-7.0.

* * * * *